United States Patent [19]

Steinmann

[11] Patent Number: 5,380,882
[45] Date of Patent: Jan. 10, 1995

[54] PHENYLACETATES AND THE USE THEREOF

[75] Inventor: Alfred Steinmann, Praroman, Switzerland

[73] Assignee: Ciba-Geigy Corporation, Ardsley, N.Y.

[21] Appl. No.: 40,230

[22] Filed: Mar. 30, 1993

[30] Foreign Application Priority Data

Apr. 1, 1992 [CH] Switzerland ............ 1054/92

[51] Int. Cl.$^6$ .............. C07D 309/12; C07D 307/20
[52] U.S. Cl. ............................. 549/420; 549/475
[58] Field of Search ................... 549/475, 420

[56] References Cited

U.S. PATENT DOCUMENTS 4,888,048 12/1989 Stroech et al.
5,034,305 7/1991 Nguyen-Kim et al. ........... 430/270
5,035,979 7/1991 Nguyen-Kim et al. ........... 430/270

FOREIGN PATENT DOCUMENTS 3722133 1/1989 Germany.

OTHER PUBLICATIONS

Kruse et al., J. Org. Chem., 43, 3548–52 (1978).
J. Kosar: "Light-Sensitive Systems", John Wiley & Sons, N.Y. 1965, pp. 339–352.
Stroech et al., CA110(25):231,643t (1989)—Abstract of DE 3,722,133.

Primary Examiner—Nicky Chan
Attorney, Agent, or Firm—William A. Teoli, Jr.

[57] ABSTRACT

The invention relates to compounds of formula I

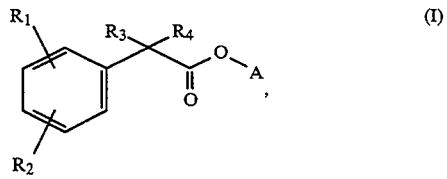

wherein A is a radical of formula

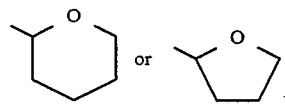

$R_1$ and $R_2$ are each independently of the other hydrogen, $C_1$–$C_4$alkyl, $C_1$–$C_4$alkoxy, halogen or a radical of formula

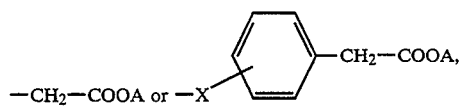

wherein X is —O—, —$CH_2$—, —$C(CH_3)_2$— or —$SO_2$—, and $R_3$ and $R_4$ are each independently of the other hydrogen, $C_1$–$C_4$alkyl or phenyl, as well as compositions comprising these compounds.

The compositions are particularly suitable for making integrated circuits.

4 Claims, No Drawings

PHENYLACETATES AND THE USE THEREOF

The present invention relates to novel phenylacetates, to compositions containing said compounds, to a process for the formation of images which comprises the use of these esters and to the use of said esters as dissolution inhibitors and of said compositions as positive resists.

For the preparation of aqueous developable photoresists it is known to mix a film-forming resin which is soluble in aqueous or aqueous-alkaline solutions with a dissolution inhibitor that greatly reduces the solubility of the mixture in an aqueous-alkaline developer. A photochemical reaction causes the dissolution inhibitor to undergo change such that, for example by the depolymerisation, acetal cleavage, orthoester cleavage or formation of a carboxylic acid from an o-quinonediazide, the photoresist is again readily soluble at the exposed areas in the developer.

Known dissolution inhibitors for positive photoresists are typically 1,2-naphthoquinonediazides (q.v. J. Kosar in "Light-Sensitive Systems", John Wiley & Sons, New York 1965, pages 339–352) in novolak resins. 1,2-Naphthoquinonediazides are photoactive and act at unexposed areas of the photoresist as dissolution inhibitors. However, they absorb very strongly in the DUV range (DUV: deep ultra-violet; range from 200 to 300 nm) and thus find only very limited utility in DUV lithography.

EP-A 367 131 and EP-A 367 132 disclose radition-sensitive compositions that consist essentially of (a) a binder which is soluble in aqueous-alkaline solutions, (b) a compound that generates a strong acid upon irradiation and (c) an ester of malonic acid or β-ketonic acid that inhibits the solubility of (a). A high radiation energy is needed for these radiation-sensitive compositions. In addition, these compositions are developed with strongly alkaline solutions.

It has now been found that specific esters of phenlacetic acid are useful dissolution inhibitors in radiation-sensitive, positive-working photoresist systems. These photoresists have high sensitivity to actinic radiation, especially in the DUV range. Moreover, they effect after exposure pronounced differences in solubility between exposed and unexposed zones so that layers with submicron resolution can be produced.

Accordingly, the invention provides novel compounds of formula I

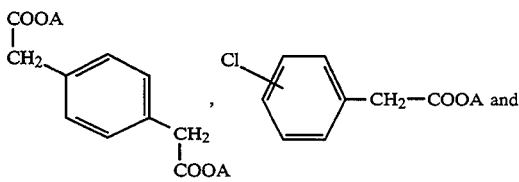

wherein A is a radical of formula

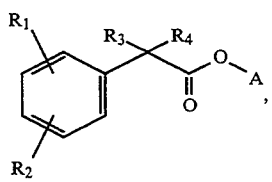

$R_1$ and $R_2$ are each independently of the other hydrogen, $C_1$–$C_4$alkyl, $C_1$–$C_4$alkoxy, halogen or a radical of formula

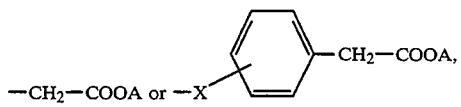

wherein X is —O—, —CH$_2$—, —C(CH$_3$)$_2$— or —SO$_2$—, and $R_3$ and $R_4$ are each independently of the other hydrogen, $C_1$–$C_4$alkyl or phenyl.

Preferred compounds of formula I, are those wherein $R_2$ is hydrogen.

Also preferred are compounds of formula I, wherein $R_1$ is hydrogen, halogen or a radical of formula —CH$_2$—COOA, and $R_3$ and $R_4$ are each independently of the other hydrogen or phenyl.

Particularly preferred compounds are those of formulae

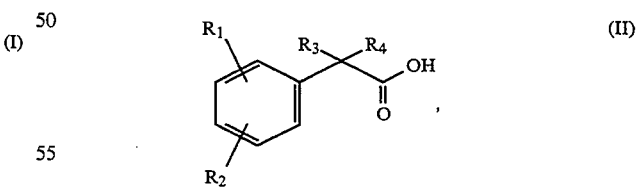

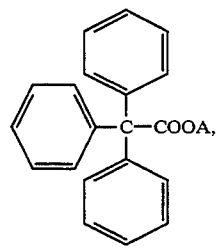

wherein A is as defined above.

$C_1$–$C_4$Alkyl substituents may be straight-chain or branched and are typically methyl, ethyl, n-propyl, isopropyl, n-butyl, sec-butyl, isobutyl or tert-butyl.

Suitable $C_1$–$C_4$alkoxy substituents may be methoxy, ethoxy, n-propoxy or n-butoxy.

Halogen will typically represent fluoro, chloro, bromo or iodo, preferably chloro and bromo. Chloro is most preferred.

The compounds of formula I may typically be prepared by reacting a compound of formula II

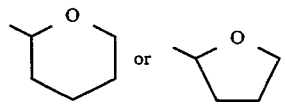

wherein $R_1$, $R_2$, $R_3$ and $R_4$ are as defined above, with 2,3-dihydrofuran or 3,4-dihydro-2H-pyran in an acid medium, in per se known manner, to compounds of formula I.

The compounds of formula II are per se known compounds and some are commercially available. Representative examples of such compounds are 2-, 3- or 4-chlorophenylacetic acid, 1,4-phenylenediacetic acid or triphenylacetic acid.

2,3-Dihydrofuran or 3,4-dihydro-2H-pyran are also commercially available.

The acid medium of the reaction solution may conveniently be prepared by adding to the reaction solution a few drops of an inorganic acid such as concentrated hydrochloric acid or sulfuric acid.

The reaction temperature is conveniently in the range from 10° to 150° C., preferably from 30° to 120° C., most preferably from 30° to 90° C. The reaction is normally carried out without a solvent. A solvent that must be inert under the reaction conditions may, however, be present. Suitable solvents include aromatic hydrocarbons, chlorinated hydrocarbons, ketones and ethers. Typical examples of such solvents are benzene, toluene, xylene, ethyl benzene, isopropyl benzene, ethylene chloride, propylene chloride, methylene chloride, chloroform, methyl ethyl ketone, acetone, cyclohexanone, diethyl ether and tetrahydrofuran.

As mentioned at the outset, the phenylacetates of formula I have dissolution inhibiting properties and are thus useful materials for positive-working photoresists. These esters have a very good inhibiting action in conventionally used binders such as novolaks or poly(hydroxy)styrenes and they then, together with acid-generating photoinitiators, form a radiation-sensitive composition that can be structured. Actinic radiation causes the acid generator to decompose and the acid which is formed cleaves the novel esters catalytically. The phenylacetate derivatives so obtained are readily soluble in aqueous-alkaline solutions. Consequently, the exposed zones can be washed out of the exposed zones of the resist composition, whereas the unexposed zones remain insoluble.

The conversion of the novel esters to carboxylic acids can be carried out with very low radiation doses. Furthermore, the difference in polarity between ester and corresponding acid is very great, resulting in substantial differences in solubility between exposed and unexposed photoresist material. This marked contrast behaviour of the resist promotes the resolution of submicron structures.

The invention also provides positive-working, radiation-sensitive compositions comprising, based on the total amounts of components A), B) and C)
A) 55 to 95% by weight of at least one binder which is soluble in aqueous-alkaline solution,
B) 4.5 to 40% by weight of at least one compound of formula I, and
C) 0.5 to 15% by weight of at least one substance which generates an acid upon exposure to actinic radiation.

The invention further relates to the use of the compounds of formula I as dissolution inhibitors in photoresist compositions.

Preferred compositions comprise, based on the total amount of components A), B) and C),
A) 65 to 90 by weight of at least one binder which is soluble in aqueous-alkaline solution,
B) 9 to 30% by weight of at least one compound of formula I, and
C) 1 to 10% by weight of at least one substance which generates an acid upon exposure to actinic radiation.

The choice of binder will depend on the field of use and the properties required therefor, for example the ability to be developed in aqueous-alkaline solvent systems, adhesion to substrates or the absorption properties.

Component A) of the novel compositions will preferably be a phenolic resin.

Particularly preferred compositions are those wherein component A) is a novolak, a poly-(4-hydroxystyrene), poly(4-hydroxy-α-methylstyrene), a copolymer of N-(4-hydroxyphenyl)maleimide with styrene, 4-hydroxystyrene, acrylic acid and methacrylic acid or a coplymer of 4-hydroxystyrene and alkoxystyrene.

The most preferred compositions are those wherein component A) is poly(4-hydroxystyrene).

A novolak used as component A) is typically derived from an aldehyde, preferably formaldehyde, acetaldehyde or furfuraldehyde, but most preferably from formaldehyde, and a phenol. The phenolic component is preferably phenol itself or also halogenated phenol, for example substituted by one or two chlorine atoms, preferably p-chlorophenol, or it is a phenol which is substituted by one or two $C_1$–$C_9$alkyl groups, o-, m- or p-cresol, a xylenol, p-tert-butylphenol or p-nonylphenol. The phenol component of the preferred novolaks may also be p-phenylphenol, resorcinol, bis(4-hydroxyphenyl)methane or 2,2-bis(4-hydroxyphenyl)propane.

To the alkaline-soluble binder used as component A) may be added further resins, as is common practice in positive systems based on diazoketones. These additional resins include typically vinyl polymers such as polyvinyl acetate, polyacrylates, polyvinyl ethers or polyvinyl pyrrolidones. Normally, however, not more than 20% by weight, based on the amount of alkali-soluble binder, of these additional resins is added.

A large number of compounds are known as radiation-sensitive components B) which, upon exposure to light, generate or release an acid. These compounds include, for example, the diazonium salts used in the diazo process, the o-quinone-diazides used in known positive-working copying compositions, or also halogen compounds which form a hydrohalic acid upon irradiation. Compounds of this type are disclosed, for example, in U.S. Pat. Nos. 3,515,552, 3,536,489 or 3,779,778, and in DE-OS 27 18 259, 22 43 621 or 26 10 842.

Particularly suitable radiation-sensitive components B) of the compositions of this invention axe photoinitiators selected from the group consisting of iodonium or sulfonium salts. Such compounds are described, for example, in "UV-Curing, Science and Technology" (Editor: S. P. Pappas, Technology Marketing Corp., 642 Westover Road, Stanford, Conn., USA).

Sulfoxonium salts can also be used as radiation-sensitive compounds. Such salts are disclosed, for example, in EP patent 35 969 or in EP-A 44 274 and 54 509. Particular mention is made of aliphatic sulfoxonium salts which absorb in the deep UV range.

It is also possible to use compounds which generate sulfonic acids when irradiated with actinic light. Such compounds are known per se and axe described, for example, in GB-A 2 120 263, EP-A 84 515; 37 512 or 58 638 and in U.S. Pat. Nos. 4,258,121 or 4,371,605.

If salts are used as the radiation-sensitive, acid-releasing components B), then said salts are preferably soluble in organic solvents. Most preferably, these salts are products with complex acids, for example with hydrofluoroboric acid, hexafluorophosphonic acid, trifluoromethanesulfonic acid, hexafluoroarsenic acid or hexafluoroantimonic acid.

The compositions of this invention may contain further conventional modifiers such as stabilisers, pigments, dyes, fillers, adhesion promoters, flow control agents, wetting agents and plasticisers. For application, the compositions may also be dissolved in suitable solvents.

The compositions of this invention have excellent suitability as coating agents for substrates of all kinds, for example wood, textiles, paper, ceramics, glass, plastics materials such as polyesters, polyethylene terephthalate, polyolefins or cellulose acetate, preferably in the form of films, and also of metals such as Al, Cu, Ni, Fe, Zn, Mg or Co, and GaAs, Si $SiO_2$, on which it is desired to produce an image by image-wise exposure.

The invention therefore also provides a process for producing positive images by I) coating a substrate with a novel radiation-sensitive composition,
II) exposing the coated substrate to irradiation with actinic light in a predetermined pattern, and
III) developing the irradiated substrate.

The substrates can be conveniently be coated by applying a solution or suspension of the novel composition to the substrate.

The choice of solvent and the concentration depends mainly on the nature of the composition and on the coating method. The solution is uniformly applied to a substrate by known coating methods, for example by spin coating, dip coating, doctor coating, curtain coating, brushing, spraying, preferably by electrostatic spraying and reverse roller coating. It is also possible to apply the light-sensitive layer to a temporary flexible support and then to coat the final substrate, for example a copper-clad circuit board, by layer transfer by means of lamination.

The add-on (layer thickness) and the nature of the substrate are contingent on the desired utility. A particular advantage of the compositions of the invention is that they can be used in widely varying layer thicknesses. This layer thickness encompasses the range from ca. 0.5 $\mu$m to more than 100 $\mu$m.

After the substrate has been coated, the solvent is normally removed by drying to give a layer of photoresist on the substrate.

After image-wise exposure of the material in conventional manner, the exposed areas of the photoresist are washed out with a developer.

The expression "imagewise" exposure will be understood as meaning exposure through a photomask which contains a predetermined pattern, for example a photographic transparency, exposure by a laser beam which is moved by computer control over the surface of the coated substrate to produce an image, as well as exposure with computer-controlled electron beams or treatment with X-rays through an absorber mask.

The light-sensitivity of the compositions of this invention extends generally from the UV region (ca. 200 nm) to ca. 600 nm and is thus very wide ranging. Especially in the DUV range (200–300 nm) the compositions of this invention exhibit excellent transparency. Suitable light sources therefore comprise a large number of very widely varying types. Point light sources as well as arrays of reflector lamps are suitable. Typical examples of such light sources are: carbon arcs, xenon arcs, mercury vapour lamps which may be doped with halogen atoms (metal halide lamps), fluorescent lamps, argon glow lamps, electronic flash lamps, photographic flood lamps, electron beams and X-rays. The distance between lamp and image material may vary, depending on the utility and the type and strength of the lamp, for example from 2 cm to 150 cm. Particularly suitable light sources are laser light sources, for example argon ion lasers or crypton ion lasers. In this type of exposure, a photomask in contact with the photopolymer layer is no longer absolutely necessary, as the controlled laser beam writes direct on to the layer. The high sensitivity of the compositions of the invention is very advantageous here and permits high writing speeds at relatively low intensities. This method can be used to make printed circuits for the electronics industry, lithographic offset plates or relief printing plates as well as photographic image recording materials.

The choice of developer depends on the type of photoresist or of the photolysis products. The developer may comprise aqueous solutions of bases to which organic solvents or mixtures thereof may be added.

Particularly preferred developers are the aqueous-alkaline solutions used for the development of naphthoquinone diazide layers. These solutions include in particular aqueous solutions of silicates, phosphates, hydroxides, carbonates and hydrogencarbonates of alkali metals. Also preferred are metal ion-free developers such as aqueous tetramethylammonium hydroxide solutions. These solutions may additionally contain minor amounts of wetting agents and/or organic solvents.

Typical organic solvents which may be added to the developer liquids are cyclohexanone, 2-ethoxyethanol, toluene, acetone, as well as mixtures of two or more of these solvents.

Possible utilities of the compositions of this invention are as photoresists in the electronics field (galvanoresist, discharge resist, solder resist), the production of printing plates such as offset plates or screen printing formes, mould etching, or as microresist in the production of integrated circuits. The possible substrates and conditions for processing the coated substrates differ accordingly.

Sheets made from polyester, cellulose acetate or plastics-coated papers are typically used for the photographic recording of information. Specially treated aluminium is used for offset printing formes, and copper-clad laminates are used for producing printed circuits, and silicon wafers are used for making integrated circuits. The layer thicknesses for photographic materials and offset printing formes axe from ca. 0.5 $\mu$m to 10 $\mu$m, and for printed circuits 1 to ca. 100 $\mu$m, and for integrated circuits 0.5 $\mu$m to 2 $\mu$m. The invention therefore relates to the use of said novel compositions as a positive photoresist for making printing formes, printed circuits or integrated circuits, as well as for silver-free photographic films.

The invention therefore further relates to the printing formes, printed circuits, integrated circuits or silver-free photographic films produced by using said compositions.

The following Examples illustrate the invention in more detail.

I. SYNTHESIS OF THE COMPOUNDS OF FORMULA I

Example A

Synthesis of tetrahydrofuran-2-yl-chlorophenylacetate 34 g (200 mmol) of 4-chlorophenylacetic acid are suspended in 42 g (600 mmol) of 2,3-dihydrofuran and 2 drops of concentrated hydrochloric acid are added to the suspension, whereupon an exothermic reaction occurs immediately and the reaction mixture becomes clear. After the reaction has subsided, the mixture is stirred for 30 minutes at 40° C. The solution is then poured into an ice-cold solution of $NaHCO_3$. The product is subsequently extracted with diethyl ether. The organic phase is dried over $Na_2SO_4$ and filtered. The solvent is then evaporated on a rotary evaporator. The residual liquid is taken up in n-hexane at 40° C., and the product is left to crystallise at 0° C. The crystals so obtained melt at 41 ° C.

Yield: 37.8 g (77% of theory).

Elemental analysis: calcd: C 59.88%; H 5.44%; Cl 14.73% found: C 59.84%; H 5.42%; Cl 14.65%

$^1$H-NMR (CDCl$_3$): 1.81–2,08 ppm, m (—CH$_2$—CH$_2$—); 3.56 ppm, s (aryl-CH$_2$—CO—); 3.79–4,05 ppm, m (—CH$_2$—O—); 6.27–6.30 ppm, m (—O—CH—O—); 7.14–7.37 ppm, m (aryl-H).

Example B

Synthesis of tetrahydropyran-2-yl-4-chlorophenylacetate 30 g (176 mmol) of 4-chlorophenylacetic acid are mixed with 42 g (500 mmol) of 3,4-dihydro-2H-pyran and 3 drops of concentrated hydrochloric acid are added to the mixture, wherepon an exothermic reaction occurs immediately and the reaction becomes clear. After the reaction has subsided, the mixture is stirred for 30 minutes at 40° C. The solution is then poured into an ice-cold solution of $NaHCO_3$. The product is subsequently extracted with diethyl ether. The organic phase is dried over $Na_2SO_4$ and filtered. The solvent is then evaporated on a rotary evaporator. The residual liquid is taken up in n-hexane at 40° C., and the product is left to crystallise at 0° C. The crystals so obtained melt at 66° C.

Yield: 30.5 g (68% of theory).

Elemental analysis: calcd: C 61.30%; H 5.94%; Cl 13.92% found: C 61.41%; H 5.90%; Cl 13.86%

$^1$H-NMR (CDCl$_3$): 1.45–1.90 ppm, m (—CH$_2$—CH$_2$—); 3.67 ppm, s (aryl-CH$_2$—CO—); 3.63–3.78 ppm, m (—CH$_2$—O—); 5.98 ppm, s (—O—CH—O—); 7.17–7.36 ppm, m (aryl-H).

Example C

Synthesis of di(tetrahydropyran-2-yl)-1,4-phenylenediacetate 19.4 g (100 mmol) of 1,4-phenylenediacetic acid are mixed with 84 g (1 mol) of 3,4-dihydro-2H-pyran and 10 drops of concentrated hydrochloric acid are added to the mixture. The solution is then stirred at 60° C. for 3 hours and working up is effected in accordance with the general procedure described in Example A. Recrystallisation from cyclohexane gives a product that melts at 103° C.

Yield: 18 g (50% of theory).

Elemental analysis: calcd: C 66.28%; H 7.23% found: C 66.33%; H 7.28%

$^1$H-NMR (CDCl$_3$): 1.52–1.76 ppm, m (—CH$_2$—CH$_2$—); 3.64 ppm, s (aryl-CH$_2$—CO—); 3.61–3.81 ppm, m (—CH$_2$—O—); 5.99 ppm, s (—O—CH—O—); 7.27 ppm, s (aryl-H).

Example D

Synthesis of tetrahydropyran-2-yl-3 -chlorophenylacetate 50 g (293 mmol) 3-chlorophenylacetic acid are mixed with 75 g (892 mmol) of 3,4-dihydro-2H-pyran and 3 drops of concentrated hydrochloric acid are added to the mixture. Working up is effected in accordance with the general procedure described in Example A, giving a product which melts at 42.5° C.

Yield: 53 g (71% of theory).

Elemental analysis: calcd: C 61.30%; H 5.94%; Cl 13.92% found: C 61.17%; H 5.87%; Cl 13.88%

$^1$H-NMR (CDCl$_3$): 1.52–1.83 ppm, m (—CH$_2$—CH$_2$—); 3.64 ppm, s (aryl-CH$_2$—CO—); 3.62–3.78 ppm, m (—CH$_2$—O—); 5.99 ppm, s (—O—CH—O—); 7.17–7.31 ppm, m (aryl-H).

Example E

Synthesis of tetrahydropyran-2-yl-2-chlorophenylacetate 50 g (293 mmol) of 2-chlorophenylacetic acid are mixed with 75 g (892 mmol) of 3,4-dihydro-2H-pyran and 3 drops of concentrated hydrochloric acid are added to the mixture. Working up is effected in accordance with the general procedure described in Example A, giving a product which melts at 38° C.

Yield: 56.7 g (76% of theory).

Elemental analysis: calcd: C 61.30%; H 5.94%; Cl 13.92% found: C 61.23%; H 5.88%; Cl 13.81%

$^1$H-NMR (CDCl$_3$): 1.42–1.78 ppm, m (—CH$_2$—CH$_2$—); 3.82 ppm, s (aryl-CH$_2$—CO—); 3.57–3.88 ppm, m (—CH$_2$—O—); 6.02:; ppm, s (—O—CH—O—); 7.17–7.44 ppm, m (aryl-H).

Example F

Synthesis of (tetrahydropyran-2-yl)-triphenylacetate 10 g (35 mmol) of triphenylacetic acid are mixed with 8.8 g (104 mmol) of 3,4-dihydro-2H-pyran and 2 drops of concentrated hydrochloric acid are added to the mixture. The solution is then stirred at 70° C. for 3 hours and working up is thereafter effected in accordance with the general procedure described in Example A. Recrystallisation from n-hexane gives a product which melts at 115° C.

Yield: 6.5 g (50% of theory).

Elemental analysis: calcd: C 80.62%; H 6.50% found: C 80.41%; H 6.48%

$^1$H-NMR (CDCl$_3$): 1.15–2.81 ppm, m (—CH$_2$—CH$_2$—); 3.24–3.63 ppm, m (—CH$_2$—O—); 6.22 ppm, s (—O—CH—O—); 7.10–7.42 ppm, m (aryl-H).

II. APPLICATION EXAMPLES

Example 1

2.5 g of the dissolution inhibitor of Example B, 7.5 g of Resin M ® P4HS [poly(4-hydroxystyrene) obtained from Maruzen Oil Comp., Japan] and 0.5 g of triphenylsulfonium trifluoromethanesulfonate are dissolved in 25 ml of cyclopentanone. This solution is filtered through a 0.5 μm filter and applied to a silicon wafer having a diameter of 76.2 mm. A homogeneous film is produced on the silicon wafer by spin coating at 3000 rpm. After drying for 60 seconds at 90° C. on a hot plate the film has a thickness of 0.9 μm. A mask is placed on the resist film by vacuum contact. The resist is then exposed through a narrow band filter with light of 254 nm wavelength. The exposure energy is 5 mJ/cm$^2$. The resist film is heated for 60 seconds at 80° C. on a hot plate and thereafter developed for 120 seconds in MF 312 [aqueous solution of tetramethylammonium hydroxide obtained from Shipley] diluted with 3 parts of water, whereupon the exposed zones dissolve in the developer (positive resist), giving 0.75 μm lines with an almost vertical wall profile.

Example 2

1 g of the dissolution inhibitor of Example C, 7.5 g of Resin M ® P4HS and 0.1 g of triphenylsulfonium trifluoromethanesulfonate axe dissolved in 20 ml of cyclopentanone. The solution is coated on to a silicon wafer as described in Example 1 to give a 1 μm film. This film is exposed through a mask with light of 254 nm wavelength at an exposure energy of 4 mJ/cm$^2$ and then heated for 60 seconds at 90° C. The latent images so obtained are developed for 140 seconds in MF 312 diluted with 4 parts of water. Submicron structures of marked resolution with high edge steepness are obtained.

Example 3

2 g of the dissolution inhibitor of Example F, 6 g of Resin M ® P4HS and 0.2 g of triphenylsulfoniumtrifluoromethanes are dissolved in 15 ml of cyclopentanone. The solution is coated on to a silicon wafer as described in Example 1 to give a 0.9 μm film. This film is exposed through a mask with light of 254 nm wavelength at an exposure energy of 7 mJ/cm² and then heated for 60 seconds at 90° C. The latent images so obtained are developed for 140 seconds in MF 312 diluted with 4 parts of water. Submicron structures of marked resolution with high edge steepness are obtained.

What is claimed is:

1. A compound of formula I

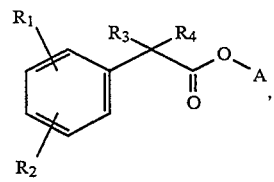

wherein A is a radical of formula

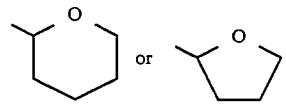

$R_1$ and $R_2$ are each independently of the other hydrogen, $C_1$-$C_4$alkyl, $C_1$-$C_4$alkoxy or halogen, and halogen $R_3$ and $R_4$ are each independently of the other hydrogen, or $C_1$-$C_4$alkyl.

2. A compound of formula I according to claim 1, wherein $R_2$ is hydrogen.

3. A compound of formula I according to claim 1, wherein $R_1$ is hydrogen or and $R_3$ and $R_4$ are hydrogen.

4. A compound according to claim 1 of formula

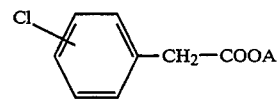

wherein A is as defined in claim 1.

* * * * *